(12) United States Patent
Nobles et al.

(10) Patent No.: US 8,197,497 B2
(45) Date of Patent: Jun. 12, 2012

(54) METHOD AND APPARATUS FOR APPLYING A KNOT TO A SUTURE

(75) Inventors: Anthony A. Nobles, Fountain Valley, CA (US); Steven E. Decker, Anaheim, CA (US); Egbert Ratering, Amsterdam (NL)

(73) Assignee: Medtronic Vascular, Inc., Santa Rosa, CA (US)

(*) Notice: Subject to any disclaimer, the term of this patent is extended or adjusted under 35 U.S.C. 154(b) by 752 days.

(21) Appl. No.: 11/455,894

(22) Filed: Jun. 19, 2006

(65) Prior Publication Data

US 2007/0010829 A1   Jan. 11, 2007

Related U.S. Application Data

(60) Provisional application No. 60/693,582, filed on Jun. 20, 2005, provisional application No. 60/709,485, filed on Aug. 19, 2005.

(51) Int. Cl.
*A61B 17/04* (2006.01)

(52) U.S. Cl. .................. 606/148; 606/139; 606/232

(58) Field of Classification Search .................. 606/148, 606/75, 139, 144, 151, 232, 72
See application file for complete search history.

(56) References Cited

U.S. PATENT DOCUMENTS

| | | | |
|---|---|---|---|
| 3,664,345 A | 5/1972 | Dabbs et al. |
| 3,665,926 A | 5/1972 | Flores |
| 3,877,434 A | 4/1975 | Ferguson et al. |
| 3,976,079 A | 8/1976 | Samuels |
| 4,291,698 A | 9/1981 | Fuchs et al. |
| 4,662,068 A | 5/1987 | Polonsky |
| 4,750,492 A | 6/1988 | Jacobs |
| 5,021,059 A | 6/1991 | Kensey et al. |
| 5,100,418 A | 3/1992 | Yoon et al. |
| 5,160,339 A | 11/1992 | Chen et al. |
| 5,171,251 A | 12/1992 | Bregen et al. |

(Continued)

FOREIGN PATENT DOCUMENTS

WO   WO 95/25470   9/1995

(Continued)

OTHER PUBLICATIONS

Invitation to Pay Additional Fees, mailed Dec. 6, 2006 in corresponding Internal Application No. PCT/US2006/023676, 6 pages.

(Continued)

*Primary Examiner* — Corrine M McDermott
*Assistant Examiner* — Mark Mashack

(57) ABSTRACT

A knot placement device allows a physician to apply a knot for securing two or more suture ends extending from an incision in a vessel or organ of a patient relative to each other in order to seal an opening in the vessel or organ. The knot placement device has a handle and an elongate shaft and a push rod slidably inserted in said shaft. A knot is disposed in the distal end of the shaft. An actuator on the handle may be depressed to distally advance said push rod relative to said shaft and thereby distally advance said knot. The knot may include a knot body having an inner cavity and a plug sized to fit securely within the inner cavity. In use, the plug may be inserted into the inner cavity of the knot body to fixedly hold two or more suture ends between the knot body and the plug.

12 Claims, 20 Drawing Sheets

U.S. PATENT DOCUMENTS

| | | | |
|---|---|---|---|
| 5,176,691 A * | 1/1993 | Pierce | 606/148 |
| 5,222,974 A | 6/1993 | Kensey et al. | |
| 5,242,459 A | 9/1993 | Buelna | |
| 5,282,827 A | 2/1994 | Kensey et al. | |
| 5,336,231 A | 8/1994 | Adair | |
| 5,364,407 A | 11/1994 | Poll | |
| 5,383,905 A * | 1/1995 | Golds et al. | 606/232 |
| 5,403,331 A | 4/1995 | Chesterfield et al. | |
| 5,423,837 A | 6/1995 | Mericle et al. | |
| 5,439,470 A | 8/1995 | Li | |
| 5,445,167 A | 8/1995 | Yoon et al. | |
| 5,452,513 A | 9/1995 | Zinnbauer et al. | |
| 5,474,572 A | 12/1995 | Hayhurst | |
| 5,514,159 A | 5/1996 | Matula et al. | |
| 5,520,702 A | 5/1996 | Sauer et al. | |
| 5,545,170 A | 8/1996 | Hart | |
| 5,584,835 A * | 12/1996 | Greenfield | 606/232 |
| 5,584,861 A | 12/1996 | Swain et al. | |
| 5,593,422 A | 1/1997 | Muijs Van de Moer et al. | |
| 5,626,590 A | 5/1997 | Wilk | |
| 5,645,553 A | 7/1997 | Kolesa et al. | |
| 5,669,917 A | 9/1997 | Sauer et al. | |
| 5,681,351 A | 10/1997 | Jamiolkowski et al. | |
| 5,700,277 A | 12/1997 | Nash et al. | |
| 5,766,183 A | 6/1998 | Sauer | |
| 5,860,990 A | 1/1999 | Nobles et al. | |
| 5,899,921 A | 5/1999 | Caspari et al. | |
| 5,902,321 A * | 5/1999 | Caspari et al. | 606/232 |
| 5,919,208 A | 7/1999 | Valenti | |
| 5,931,844 A * | 8/1999 | Thompson et al. | 606/144 |
| 5,935,149 A | 8/1999 | Ek | |
| 5,951,590 A | 9/1999 | Goldfarb | |
| 6,015,428 A | 1/2000 | Pagedas | |
| 6,033,430 A * | 3/2000 | Bonutti | 606/232 |
| 6,066,160 A | 5/2000 | Colvin et al. | |
| 6,077,277 A | 6/2000 | Mollenauer et al. | |
| 6,086,608 A * | 7/2000 | Ek et al. | 606/232 |
| 6,099,553 A | 8/2000 | Hart et al. | |
| 6,110,185 A | 8/2000 | Barra et al. | |
| 6,117,144 A | 9/2000 | Nobles et al. | |
| 6,126,677 A | 10/2000 | Ganaja et al. | |
| 6,159,234 A | 12/2000 | Bonutti et al. | |
| 6,174,324 B1 | 1/2001 | Egan et al. | |
| 6,187,026 B1 | 2/2001 | Devlin et al. | |
| 6,200,329 B1 * | 3/2001 | Fung et al. | 606/232 |
| 6,203,565 B1 | 3/2001 | Bonutti et al. | |
| 6,217,591 B1 | 4/2001 | Egan et al. | |
| 6,432,115 B1 | 8/2002 | Mollenauer et al. | |
| 6,468,293 B2 * | 10/2002 | Bonutti et al. | 606/232 |
| 6,547,725 B1 | 4/2003 | Paolitto et al. | |
| 6,562,052 B2 | 5/2003 | Nobles et al. | |
| 6,716,243 B1 | 4/2004 | Colvin et al. | |
| 6,733,509 B2 | 5/2004 | Nobles et al. | |
| 6,855,157 B2 | 2/2005 | Foerster et al. | |
| 7,083,638 B2 | 8/2006 | Foerster | |
| 7,090,690 B2 | 8/2006 | Foerster et al. | |
| 7,172,595 B1 * | 2/2007 | Goble | 606/86 A |
| 7,220,266 B2 | 5/2007 | Gambale | |
| 7,326,221 B2 | 2/2008 | Sakamoto et al. | |
| 7,399,304 B2 | 7/2008 | Gambale et al. | |
| 7,491,217 B1 | 2/2009 | Hendren | |
| 7,637,926 B2 | 12/2009 | Foerster et al. | |
| 7,993,368 B2 * | 8/2011 | Gambale et al. | 606/232 |
| 2002/0087178 A1 * | 7/2002 | Nobles et al. | 606/167 |
| 2002/0111653 A1 | 8/2002 | Foerster | |
| 2002/0128684 A1 | 9/2002 | Foerster | |
| 2003/0078601 A1 | 4/2003 | Shikhman et al. | |
| 2003/0149448 A1 | 8/2003 | Foerster et al. | |
| 2003/0167062 A1 | 9/2003 | Gambale et al. | |
| 2003/0171760 A1 | 9/2003 | Gambale | |
| 2003/0181926 A1 | 9/2003 | Dana et al. | |
| 2003/0208209 A1 | 11/2003 | Gambale et al. | |
| 2004/0093031 A1 | 5/2004 | Burkhart et al. | |
| 2004/0097968 A1 | 5/2004 | Shikhman et al. | |
| 2004/0098050 A1 | 5/2004 | Foerster et al. | |
| 2004/0181238 A1 * | 9/2004 | Zarbatany et al. | 606/108 |
| 2004/0210238 A1 | 10/2004 | Nobles et al. | |
| 2004/0260298 A1 | 12/2004 | Kaiseer et al. | |
| 2005/0033319 A1 | 2/2005 | Gambale et al. | |
| 2005/0240226 A1 | 10/2005 | Foerster et al. | |
| 2005/0261708 A1 | 11/2005 | Pasricha et al. | |
| 2005/0261710 A1 | 11/2005 | Sakamoto et al. | |
| 2005/0277986 A1 | 12/2005 | Foerster et al. | |
| 2005/0288688 A1 | 12/2005 | Sakamoto et al. | |
| 2006/0047314 A1 * | 3/2006 | Green | 606/232 |
| 2006/0271074 A1 | 11/2006 | Ewers et al. | |
| 2007/0005081 A1 * | 1/2007 | Findlay et al. | 606/148 |
| 2007/0032798 A1 | 2/2007 | Pantages et al. | |
| 2008/0234729 A1 | 9/2008 | Page et al. | |

FOREIGN PATENT DOCUMENTS

| | | |
|---|---|---|
| WO | WO 98/12970 | 4/1998 |
| WO | WO 00/02489 | 1/2000 |

OTHER PUBLICATIONS

International Search Report and Written Opinion for PCT/US2006/023676, mailed on Jun. 6, 2007 in 14 pages.

* cited by examiner

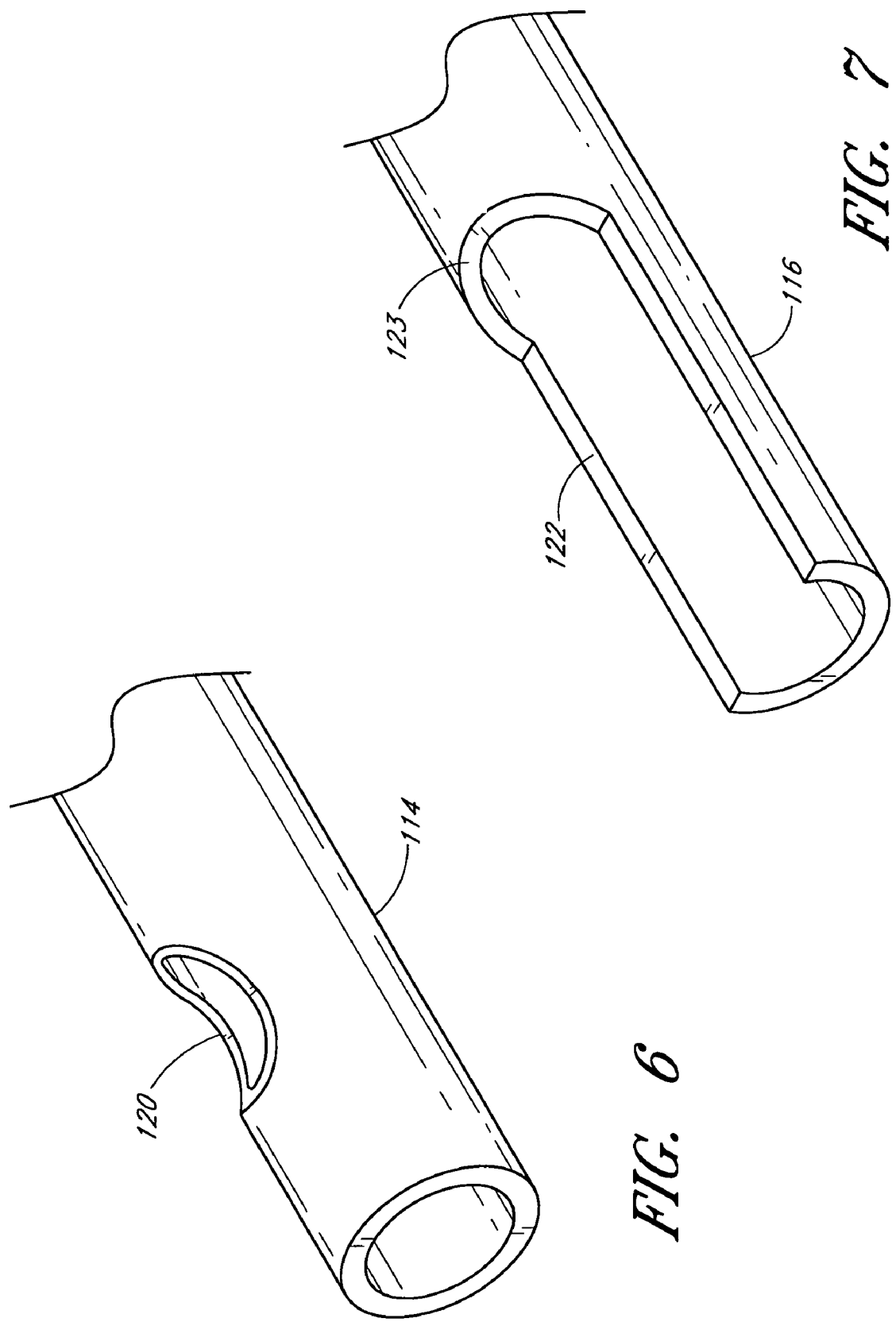

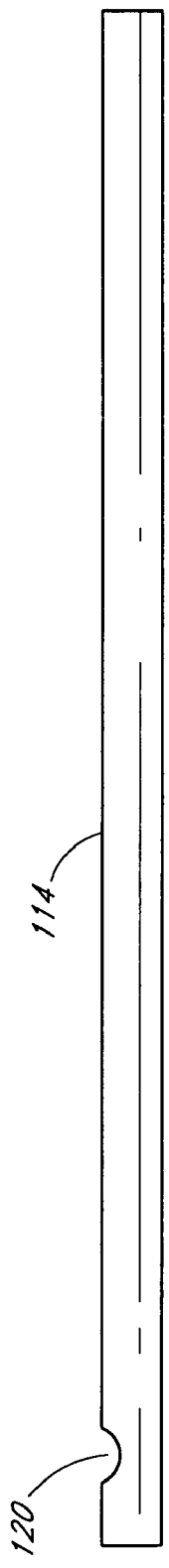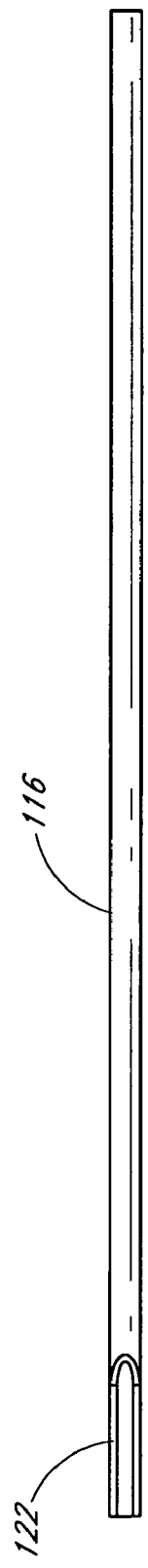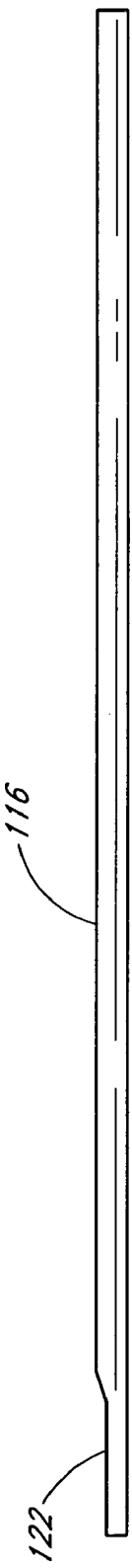

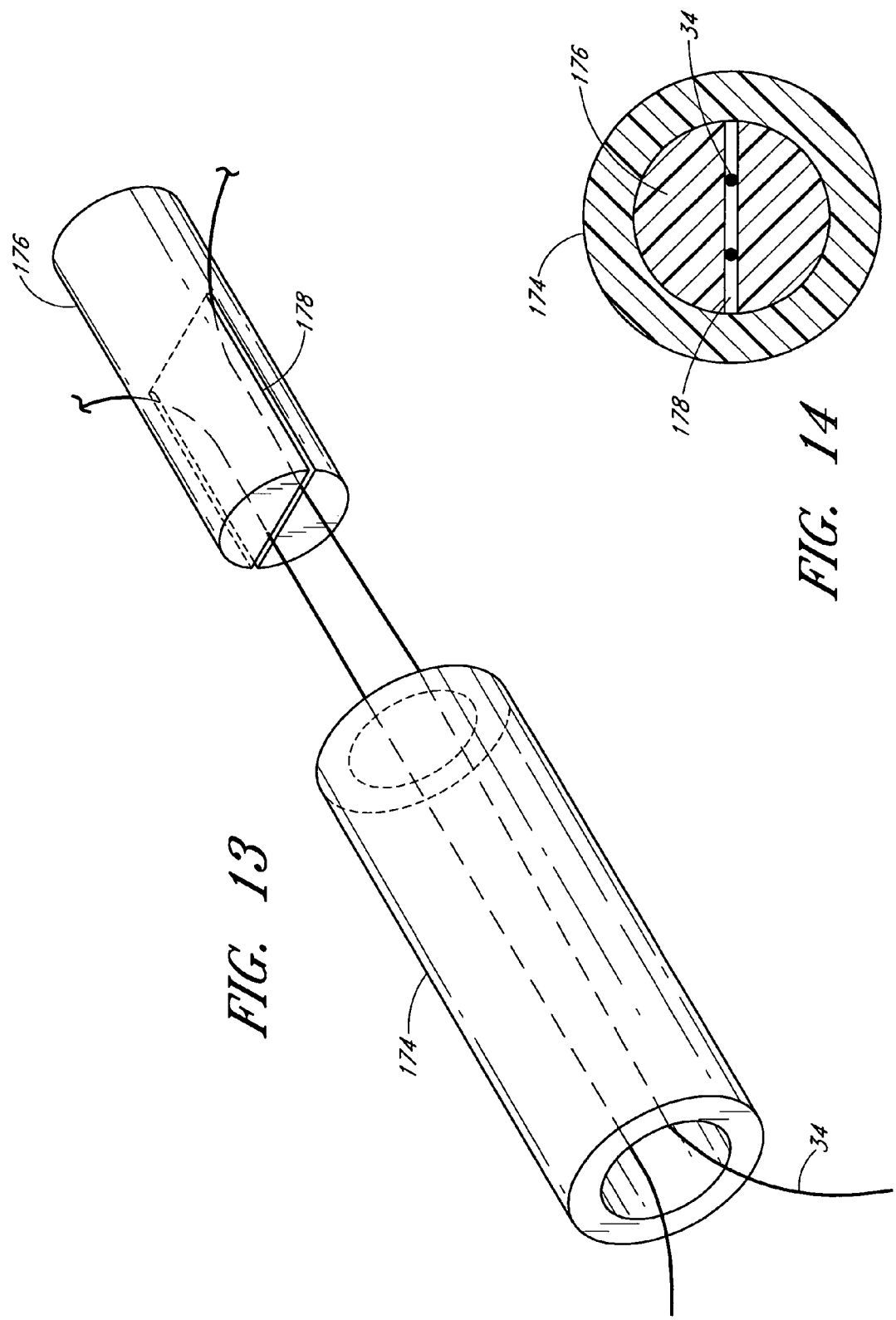

METHOD AND APPARATUS FOR APPLYING A KNOT TO A SUTURE

CROSS-REFERENCE TO RELATED APPLICATIONS

This application claims the benefit of U.S. Provisional Application No. 60/693,582, filed on Jun. 20, 2005 and U.S. Provisional Application No. 60/709,485, filed on Aug. 19, 2005, the entirety of which are hereby incorporated by reference.

BACKGROUND OF THE INVENTION

1. Field of the Invention

Certain embodiments of the invention relate to suturing incisions and, more specifically, to the use of sutures for closing incisions in vessels or in organs within a body.

2. Description of the Related Art

Surgeons frequently encounter the need to close incisions, wounds, or otherwise joining tissue portions with a suture. After passing the suture through the tissue portions, the surgeon must tie and cinch the suture to draw the tissue portions together and prevent them from separating. When sutures are tied in a region having restricted access, such as the end of a tissue tract leading to an artery, the surgeon is presented with special challenges. Sutures can often be difficult to handle, thereby increasing the time that it takes for a surgeon to tie a suture. Accordingly, what is needed is a faster and more effective way to tie and cinch a suture.

SUMMARY OF THE INVENTION

Certain embodiments of the present invention describe various methods and apparatus for applying a knot to a suture. When two ends of a suture extend away from an incision in a vessel or an organ of a patient, the preferred embodiments provide a method and apparatus for desirably securing two suture portions relative to each other, with the securement being provided adjacent the incision to hold the incision closed. As used herein, the term "knot" is a broad term encompassing its ordinary meaning and includes, but is not limited to, any arrangement, component or combination of components designed to fixedly hold a suture relative to a desired knot location. More preferably, a knot may encompass any arrangement, component or combination of components designed to fixedly hold two portions of a suture relative to a desired knot location. Thus, a knot encompasses arrangements in which suture portions are tied, and also encompasses arrangements in which suture portions are securely held relative to one another without being tied. The desired knot location may include an incision, a wound, a body cavity, an opening in body tissue, and two adjacent body tissues wherein the space between the two adjacent body tissues is desired to be closed. The two suture portions may be portions of the same suture or different sutures.

In one embodiment, a knot placement device is provided. The knot placement device preferably includes a handle and a shaft. The handle comprises a proximal end and a distal end. The shaft comprises a proximal end and a distal end which extends distally from the handle. A knot is disposed, either partially or entirely, within the distal end of the shaft. The handle further comprises an actuator which places the knot about two suture portions to fix the two suture portions relative to one another.

In one embodiment, the actuator may be a thumb or finger button designed for cooperation with a cam. The cam may be fixedly attached to a push rod. The push rod is concentrically and slidably disposed within an outer tube. The outer tube may be fixedly attached to a distal end portion of the handle. The knot placement device may further comprise an intermediate tube concentrically and slidably disposed between the outer tube and the push rod. The intermediate tube comprises a proximal end and a distal end. The proximal end of the intermediate tube may be located between the cam and the distal end portion of the handle. Partial depression of the actuator distally advances the push rod. At some degree of depression, the actuator contacts the proximal end of the intermediate tube, thus distally advancing the intermediate tube.

In one embodiment, the intermediate tube may comprise a key. The outer tube, the end portion, or both may include a keyway designed for cooperation with the key. The key and associated keyway maintain rotational alignment of the intermediate tube relative to the outer tube. In another embodiment, the intermediate tube may comprise a keyway, and the outer tube or the end portion may comprise a key.

In one embodiment, the shaft comprises an outer tube having a proximal end and a distal end. The outer tube may comprise an aperture located near its distal end. The shaft may further comprise an intermediate tube concentrically and slidably disposed within the outer tube. The intermediate tube may comprise a slot located at or near its distal end. A push rod may be concentrically and slidably disposed within the intermediate tube and outer tube. A knot is disposed, either partially or entirely, within the distal end of the outer tube.

In one embodiment, the knot comprises a plug and a knot body, wherein the plug is adapted to be received within the knot body. The plug comprises a proximal end and a distal end, and may be of a generally constant outer diameter. Alternatively, the plug may be generally tapered from the proximal end to the distal end. Alternatively, the plug may comprise a portion of generally constant outer diameter and a generally tapered portion. The plug may also comprise a rounded or chamfered edge at the distal end. The plug may also comprise a shoulder located near the proximal end having an increased outer diameter.

The knot body may be generally tubular and comprise a proximal end, a distal end, and a longitudinal axis. The knot body may be of a generally constant inner diameter and outer diameter. Alternatively, the inner diameter, the outer diameter, or both may generally taper along the longitudinal axis of the knot body. Alternatively, the inner diameter, the outer diameter, or both may generally taper along a portion of the longitudinal axis and may be of a generally constant inner diameter, outer diameter or both over a portion of the longitudinal axis.

The knot body may comprise an opening at its distal end. The opening at the distal end of the knot body may, in some embodiments, be of a reduced diameter. The knot body may also comprise an opening at the proximal end. The opening at the proximal end may, in some embodiments, be of a reduced diameter. The knot body may further comprise protrusions from the inner surface of the knot body toward the longitudinal axis.

In one embodiment, the knot body may be located distally from the plug within the outer tube. In another embodiment, the plug may be located distally from the knot body within the outer tube.

In one embodiment, a method is provided for placing a knot on a suture to close an opening in the body. A pair of suture ends is passed through a threader. The threader is pulled through a passage in the distal end of a shaft of a knot placement device. As the threader is pulled through the passage, the suture portions are drawn through the passage, and desirably positioned within a knot body positioned at a distal end of the shaft. Tension may be applied to the suture portions as the knot placement device is slid along the suture portions toward a pair of tissue portions. The knot placement device is advanced until the knot body or distal end of the device is in contact with a tissue portion. An actuator is depressed, which in one embodiment advances a push rod within the shaft against a plug and advances the plug into the knot body. This traps the suture between the plug and the knot body. In one preferred embodiment, continued depression of the actuator causes an intermediate tube to be advanced to sever the suture portions, eject the knot from the placement device, or both. The device is then retracted from the patient.

In one embodiment, after the knot is ejected and before the suture ends are severed, the push rod is positioned substantially flush with a distal end of the shaft. The distal end of the shaft is used to push the knot toward the tissue portions to further secure the knot and draw the tissue portions closer together.

BRIEF DESCRIPTION OF THE DRAWINGS

FIG. 6 is a perspective view of the distal end of the outer tube of the knot placement device of FIG. 2.

FIG. 7 is a perspective view of the distal end of the intermediate tube of the knot placement device of FIG. 2.

FIG. 8 is a side view of the outer tube of FIG. 6.

FIG. 9a is a top view of the intermediate tube of FIG. 7.

FIG. 9b is a side view of the intermediate tube of FIG. 7.

FIG. 13 is a perspective view of another embodiment of a knot.

FIG. 14 is a transverse cross-sectional view of the knot of FIG. 13.

FIG. 18b is a cross-sectional side view of the knot of FIG. 18a.

DETAILED DESCRIPTION OF THE PREFERRED EMBODIMENTS

The preferred embodiments of the present invention described below relate particularly to applying a knot to two portions of a suture. More particularly, the preferred embodiments relate to applying a knot to portions of a suture extending from a treatment location of a patient. The treatment location may be any desired location, such as an arterial vessel, a venous vessel, or any other body tissue. Suture ends may be the ends of the same suture or may be the ends of separate sutures.

Figure 1:
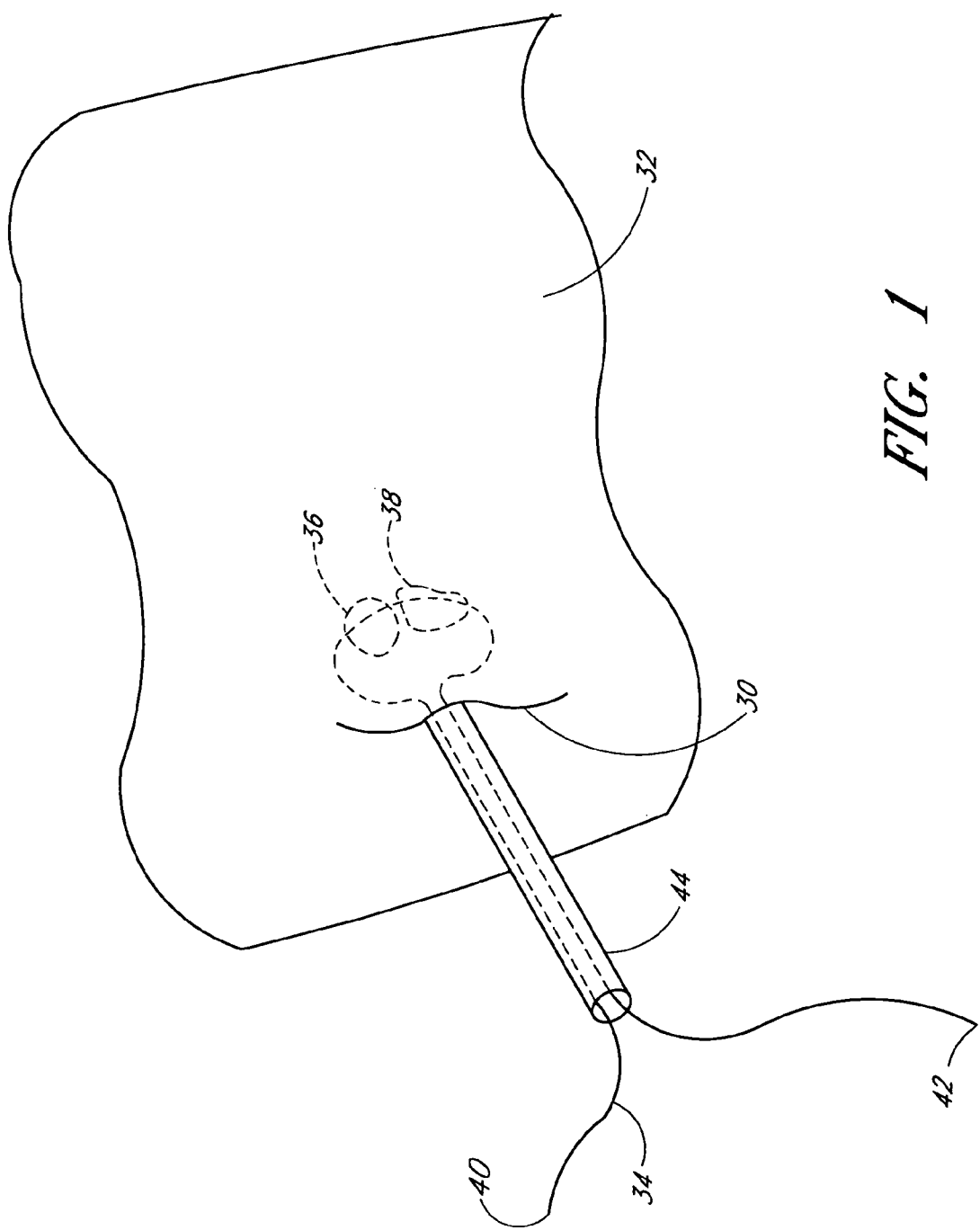
FIG. 1 is a perspective view of a wound site having a pair of suture ends extending therefrom.

FIG. 1 illustrates the wound site of a patient wherein it may be desired to apply a knot to a suture. More particularly, FIG. 1 shows an incision 30 in the patient's skin used to perform any sort of treatment on the patient. After the patient has been treated, a suture 34 is introduced into the patient through a catheter sheath introducer (CSI) 44 for the purpose of drawing together tissue portions 36 and 38 (shown in phantom in FIG. 1). Two end portions 40 and 42 of the suture 34 extend from the tissue portions 36, 38, respectively, which may, for example, be the result of a wound or an internal incision in a blood vessel or an organ. The suture 34 may be introduced into the patient by any suitable manner, including those described in U.S. Pat. Nos. 5,860,990, 6,117,144, 6,562,052, and Applicant's application Ser. No. 11/235,751 filed Sep. 27, 2005, now U.S. Publication No. 2006-0069397, all of which are hereby incorporated by reference in their entirety. Suture 34 may be, but is not limited to, 0.007" diameter biodegradable material or non-biodegradable materials, such as polypropylene. The suture 34 may also be braided or may be of other materials and have other configurations. The suture 34 in FIG. 1 is shown extending from a catheter sheath introducer 44. The suture 34 may also extend directly from an incision in a patient.

Figure 2:
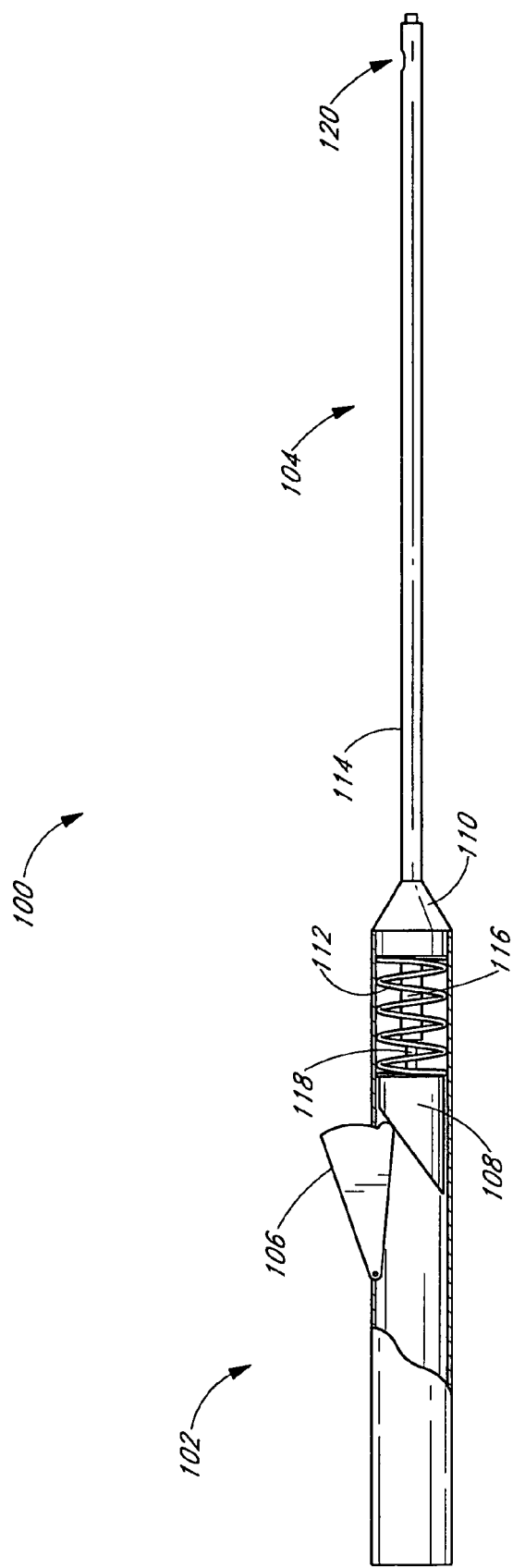
FIG. 2 is a side view of one embodiment of a knot placement device.
Figure 3:
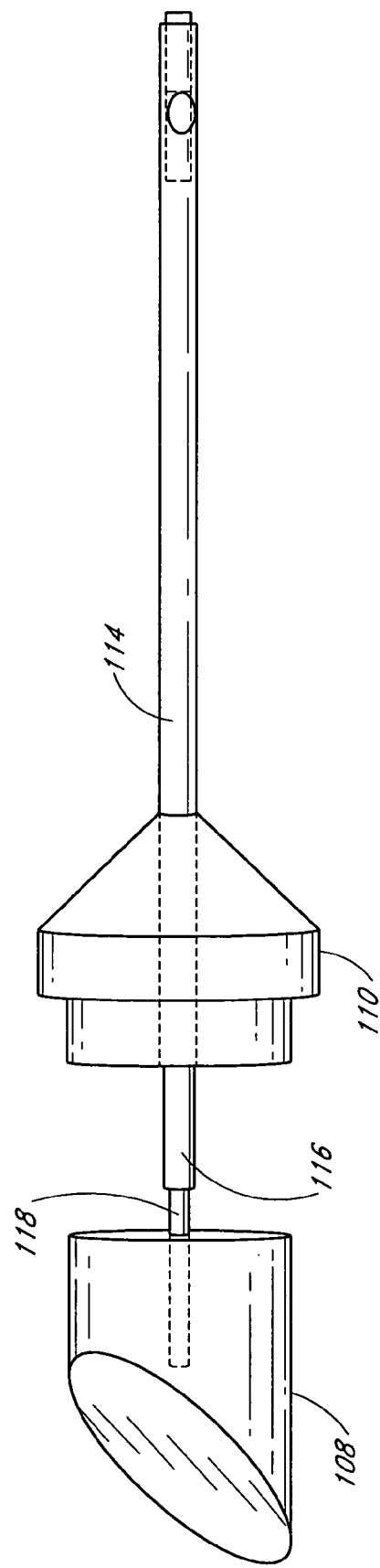
FIG. 3 is a side view of the shaft, cam, and distal end portion of the knot placement device of FIG. 2 with a knot shown within the shaft in phantom.
Figure 4:
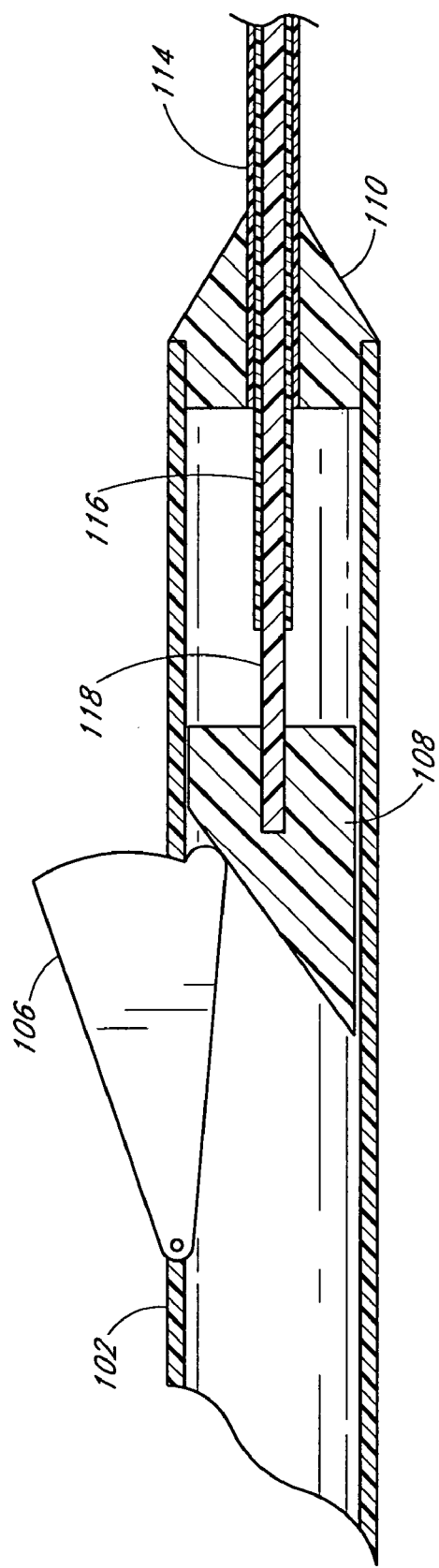
FIG. 4 is a partial cross-sectional side view of the handle of the knot placement device of FIG. 2.

FIGS. 2-4 illustrate one embodiment of a knot placement device 100 that may be used to apply a knot to the suture 34. The knot placement device 100 comprises a handle 102 and a shaft 104 extending distally from the handle. The handle 102 preferably comprises an elongate tubular body extending from a proximal end to a distal end, and comprises an actuator 106 and a distal end portion 110. The handle 102 may further comprise a cam 108 and a spring 112, shown in its rest position, disposed between the cam 108 and end portion 110. The actuator 106 may be a thumb or finger button in contact with the cam 108. End portion 110 may be fixedly attached to an outer tube 114 by glue, press fit, injection molding, or other suitable means know to one of ordinary skill in the art. An intermediate tube 116 may be concentrically and slidably disposed within the outer tube 114. A push rod 118 is concentrically and slidably disposed within the intermediate tube 116 and fixedly attached to the cam 108. It should be appreciated that it is contemplated that the knot placement device 100 does not necessarily comprise an intermediate tube 116; however its inclusion provides certain benefits.

As shown in FIG. 4, depression of the actuator 106 causes the cam 108 to move distally, compressing the spring 112 (not shown), thereby moving the push rod 108. After traveling for a certain desired distance, the cam 108 engages a proximal end of the intermediate tube 116, causing the intermediate tube 116 to also move distally. Upon release of the actuator 106, the spring 112 expands to move the cam 108 and the push rod 118 proximally. In the illustrated embodiment, the intermediate tube 116 is freely slidable over the push rod 118.

In one embodiment, not shown, the cam 108 comprises a detent in the surface which contacts the actuator 106. The detent may signal to the user a specific degree of advancement of the push rod 118, the intermediate tube 116, or both. For example, the detent may signal that the push rod has been advanced sufficiently far to insert the plug into the knot body, as described below. The detent may also indicate travel up until, but not including, the point at which the cam 108 engages the intermediate tube 116. The detent may be shaped so as to prevent the actuator 106 from returning to its original position. The cam may comprise multiple detents to indicate multiple increments of travel. To return the actuator to its initial position, the actuator and cam may include a mechanism such that after the actuator is fully depressed, the actuator may automatically return to its initial position. Alternatively, the actuator may have a locked configuration, either at one of the detents or in a fully depressed configuration, and the handle may include a mechanism by which a second actuator is used to release the cam and actuator to return to their initial positions. Further details of such mechanisms are found in application Ser. No. 11/235,751 filed Sep. 27, 2005, the entirety of which is hereby incorporated by reference.

In one embodiment, not shown, the intermediate tube 116 may comprise a keyway and the outer tube 114, the end portion 110, or both may comprise a key. Alternatively, the intermediate tube 116 may comprise a key and the outer tube 114, the end portion 110, or both may comprise a keyway. Providing such a key and keyway may be used to keep the intermediate tube 116 aligned with the outer tube. Other embodiments are contemplated to maintain rotational alignment of the intermediate tube, such as rotationally fixing the intermediate tube relative to the push rod. Providing such a key and keyway may also be used to constrain the range of sliding movement of the intermediate tube 116.

Figure 5:
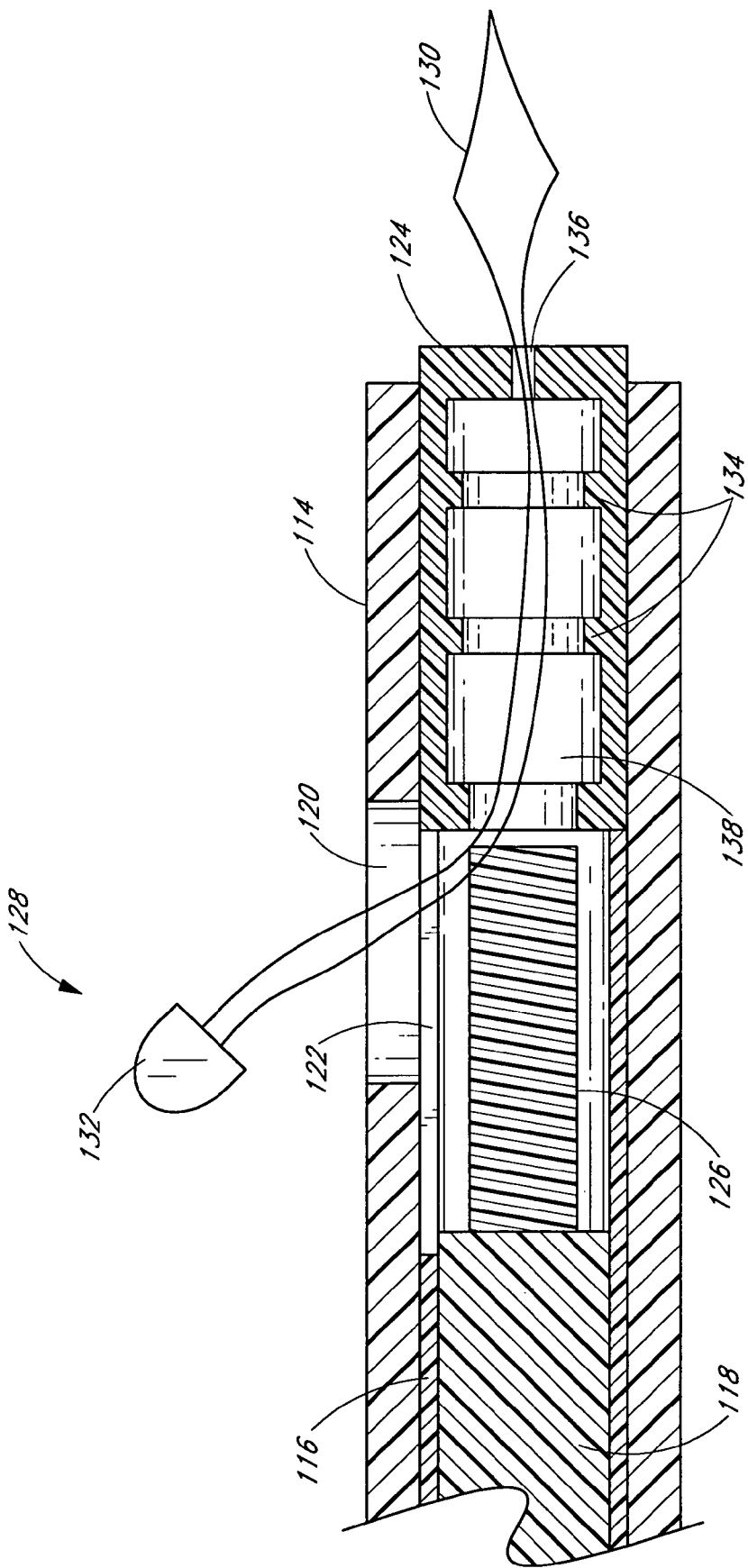
FIG. 5 is a partial cross-sectional side view of the distal end of the shaft of the knot placement device of FIG. 2.

As shown in FIG. 5, a knot, comprising a knot body 124 and a plug 126, is disposed within the outer tube 114 at its distal end. The knot body 124 may be retained in the outer tube 114 by a net fit or press fit. Alternatively, the fit between the knot body 124 and the outer tube 114 may not retain the knot body 124 in the outer tube 114. The knot body 124 is preferably at the distal end of the outer tube 114, and may protrude slightly distal to the distal end of outer tube 114. The plug 126 is positioned proximal to the knot body 124, and may be slidably disposed within the intermediate tube 116, having a distal end located proximally from the knot body and distally from the push rod 118. The plug 126 has an outer dimension configured to be inserted into an inner cavity of the knot body 124. The intermediate tube 116 is preferably sized and positioned such that its distal end may abut knot body 124.

As shown in FIGS. 5, 6 and 8, the outer tube 114 may include a side hole 120 near its distal end. As shown in FIGS. 5, 7, 9a and 9b, the intermediate tube 116 may include a slot 122 extending proximally from its distal end, forming a C-shaped cross section. At a proximal end of the slot 122, a sharpened cutting surface 123 may be provided to cut suture 34, as described below. The slot 122 is preferably rotationally aligned with the opening 120, such as by using a key/keyway arrangement as described above. The slot 122 is also preferably axially aligned with the opening 120, although it will be appreciated that because of the ability of the intermediate tube 116 to slide relative to push rod 118, the intermediate tube may be positioned with the slot 122 proximal to the opening 120 and its distal end proximal to the plug 126. The slot 122 may also be spaced from the distal end of the intermediate tube, such that the distal end of the tube still forms a complete circle in cross-section. The outer tube 114, intermediate tube 116 and push rod 118 may be made of any suitable material, including but not limited to metals, plastics, and a combination of metals and plastics.

As shown in FIG. 5, in a preloaded configuration, the knot placement device 100 may include a threader 128 comprising a tab 132 and a looped wire 130 passing through the side hole 120 in the outer tube 114. The wire 130 preferably extends through the slot 122 located in the intermediate tube 116, and through knot body 124, exiting through opening 136 at the distal end of the knot body 124. The threader 128 is used to load the suture into the knot placement device as described below. The threader 128 also prevents the knot body 124 from escaping from the placement device 100 when the knot body is provided with an outer dimension of the same or smaller size than the inner wall of the outer tube 114.

Figure 10:
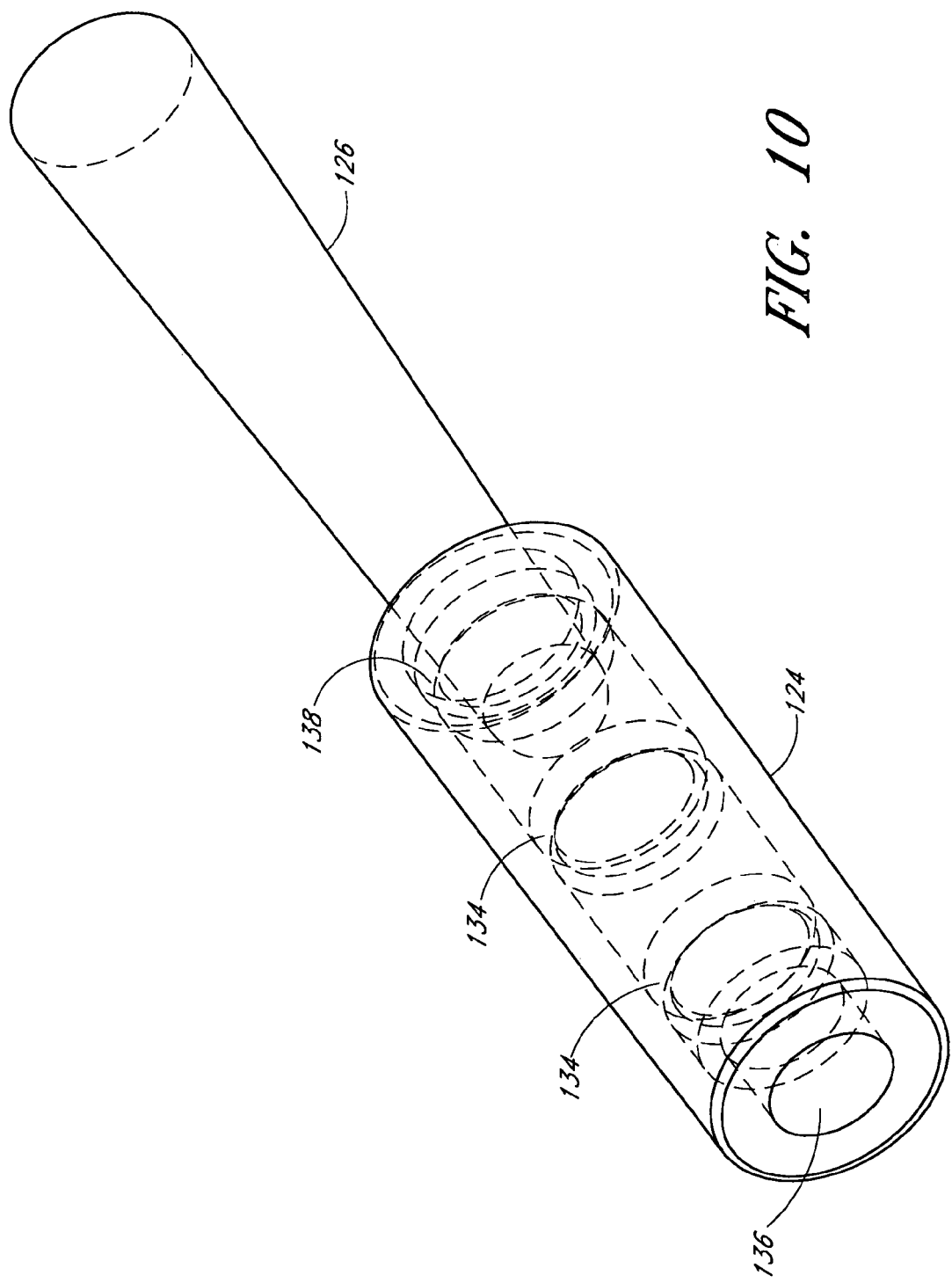
FIG. 10 is a perspective view of one embodiment of a knot.

With reference to FIGS. 5 and 10, the knot body 124 may be generally tubular and comprise a proximal end, a distal end, and a longitudinal axis. The knot body 124 preferably further defines an inner cavity and comprises an opening 136 at its distal end. The knot body may be of a generally constant inner diameter and outer diameter. Alternatively, the inner diameter, the outer diameter, or both may generally taper along the longitudinal axis of the knot body. Alternatively, the inner diameter, the outer diameter, or both may generally taper along a portion of the longitudinal axis and may be of a generally constant inner diameter, outer diameter or both over a portion of the longitudinal axis.

The opening 136 at the distal end of the knot body may, in some embodiments, be of a reduced diameter relative to an inner cavity of the knot body 124. The knot body also comprises an opening 138 at the proximal end. The opening 138 at the proximal end may, in some embodiments, be of a reduced diameter relative to an inner cavity of the knot body 124. The knot body may further comprise protrusions 134 extending from the inner surface of the knot body 124 toward the longitudinal axis. Protrusions 134 may be formed as rings as illustrated, or as spirals, spikes, bumps, or other suitable structures or combinations of structures.

Referring to FIGS. 5 and 10, in one embodiment, the knot body 124 may be located distally from the plug 126 within the outer tube 114. The plug is preferably sized to be inserted into the inner cavity of the knot body 124, and may have a tapered configuration as shown in FIG. 10. Alternatively, the plug 126 may have a constant cross-section over a majority of its length, such as shown in FIG. 5, with a tapered, chamfered or rounded distal end for facilitating insertion into the knot body 124. The outer dimension of the plug 126 may be slightly larger than the inner dimension of the cavity of the knot body 124, such that when the plug is inserted into the cavity, a relatively secure fit is provided between the two. The protrusions 134 within the knot body further facilitate the relative securement. The plug 126 may also comprise indentations, not shown, for receiving the protrusions 134 to secure the plug 126 more surely in the knot body 124. Other embodiments are contemplated wherein protrusions are formed on the plug 126 with or without indentations formed in the inner cavity of the knot body 124. It is also contemplated that in some embodiments both the plug 126 and the knot body 124 may comprise protrusions and indentations, respectively. In certain embodiments, insertion of the plug 126 into the knot body 124 may cause the knot body 124 to slightly expand. Both the knot and the knot body may be formed of any suitable resilient materials, and in one embodiment, are made from the same material as the suture, more preferably polypropylene.

Figure 19:
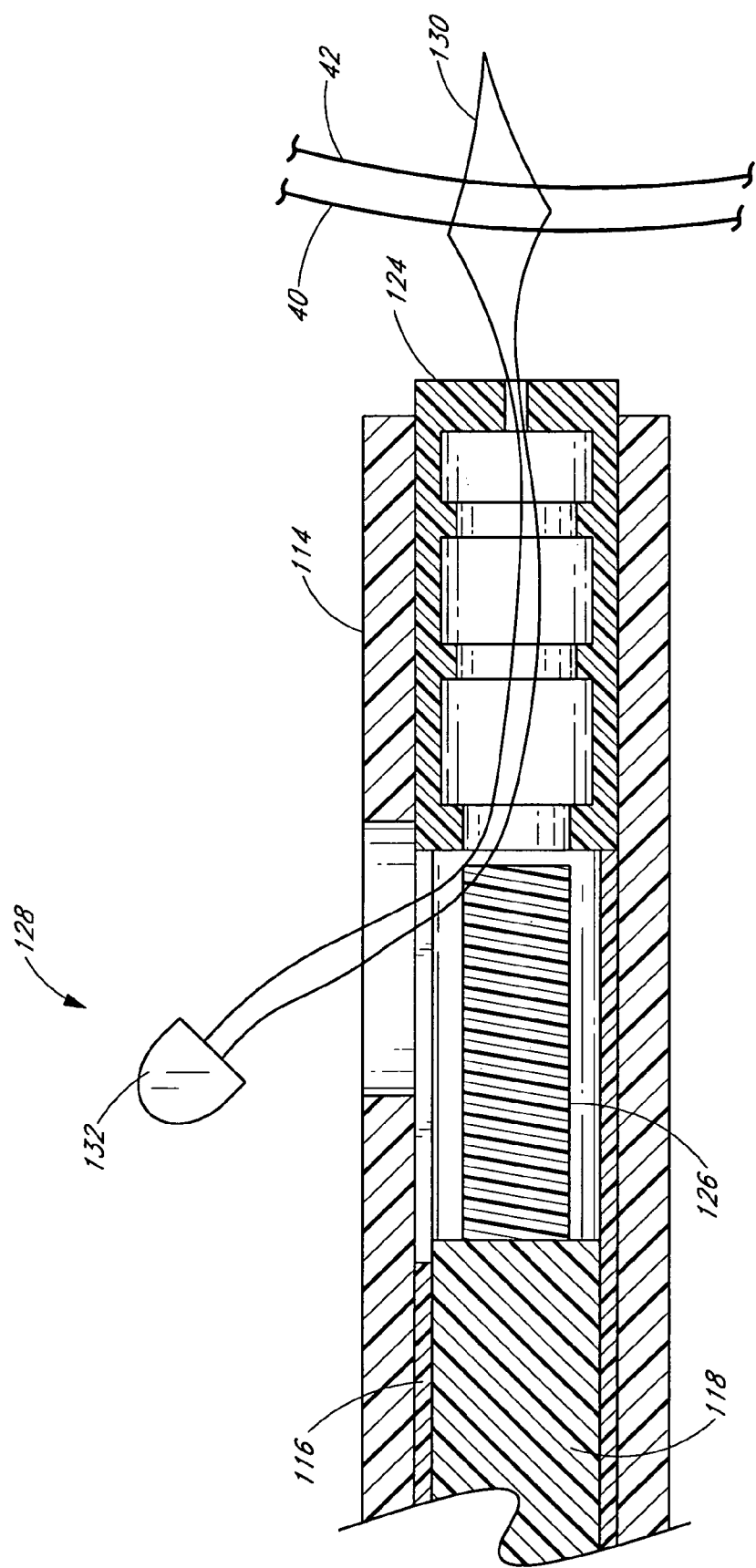
FIG. 19 is a partial cross-sectional view of a knot placement device, with suture ends passing through a threader.
Figure 20:
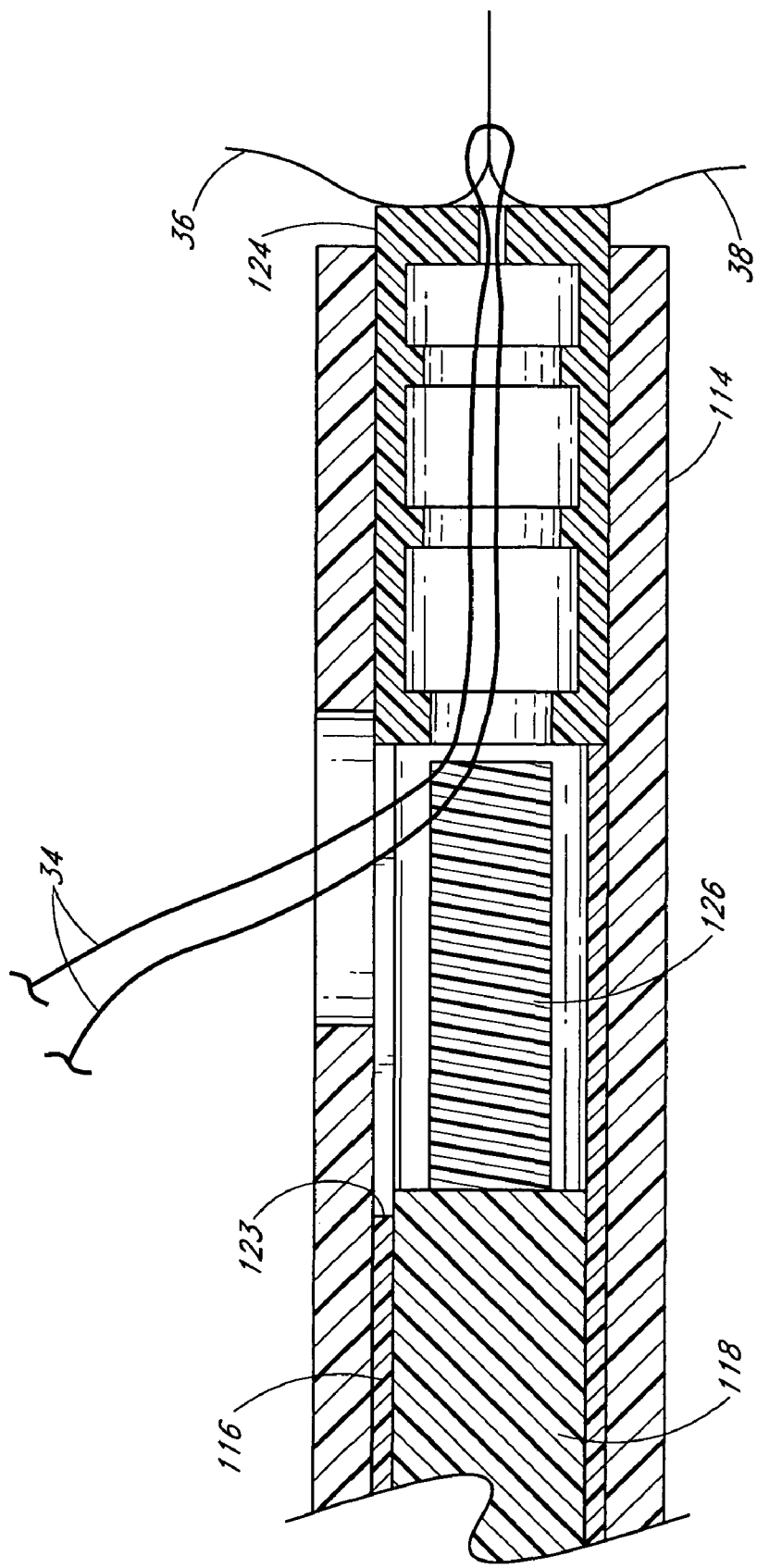
FIG. 20 illustrates the device of FIG. 19 having two suture portions passing therethrough, with the distal end of the device in contact with a tissue portion.
Figure 21:
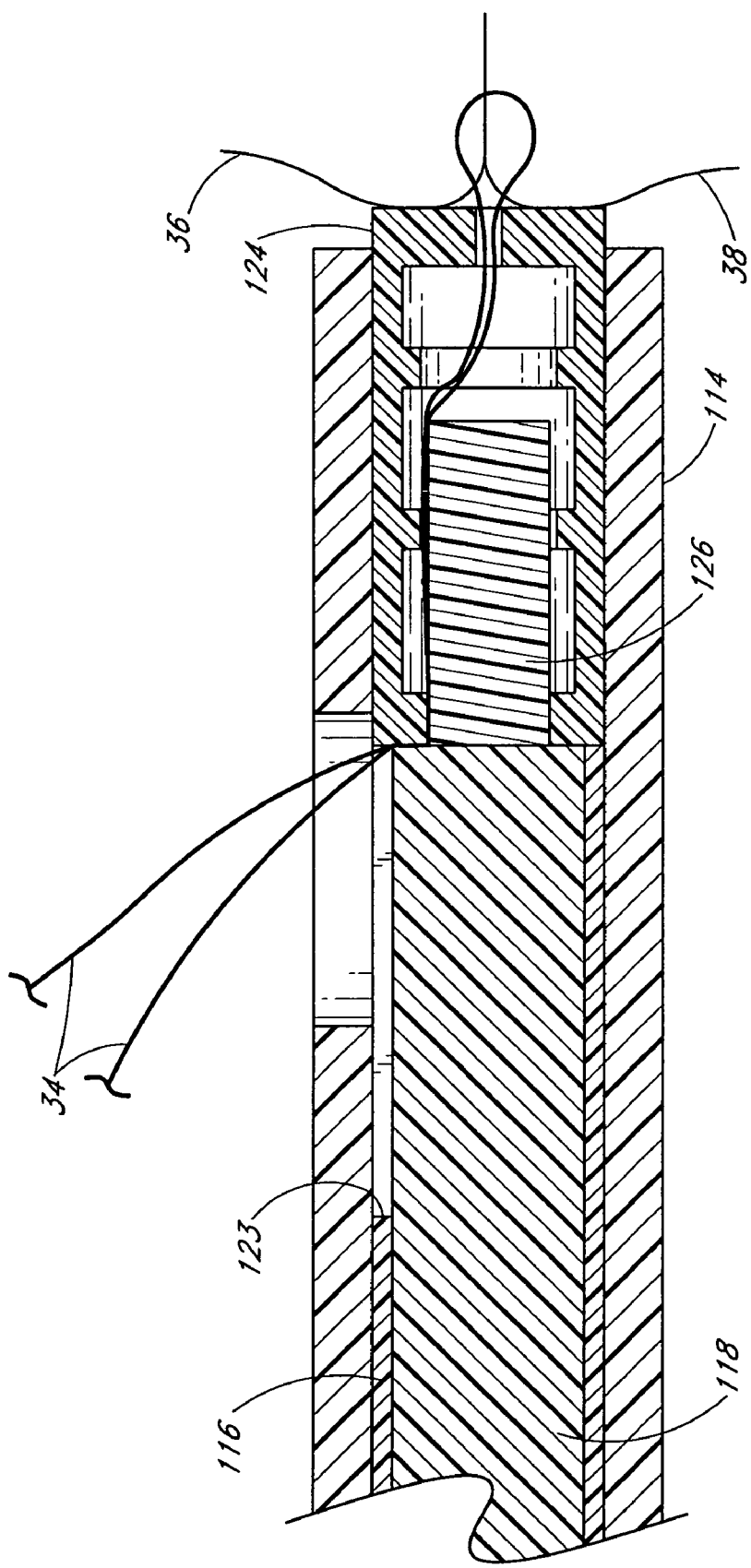
FIG. 21 illustrates the device of FIGS. 19-20 with the push rod being advanced until the plug is inserted into the knot body, trapping the suture portions between the plug and knot body.
Figure 22:
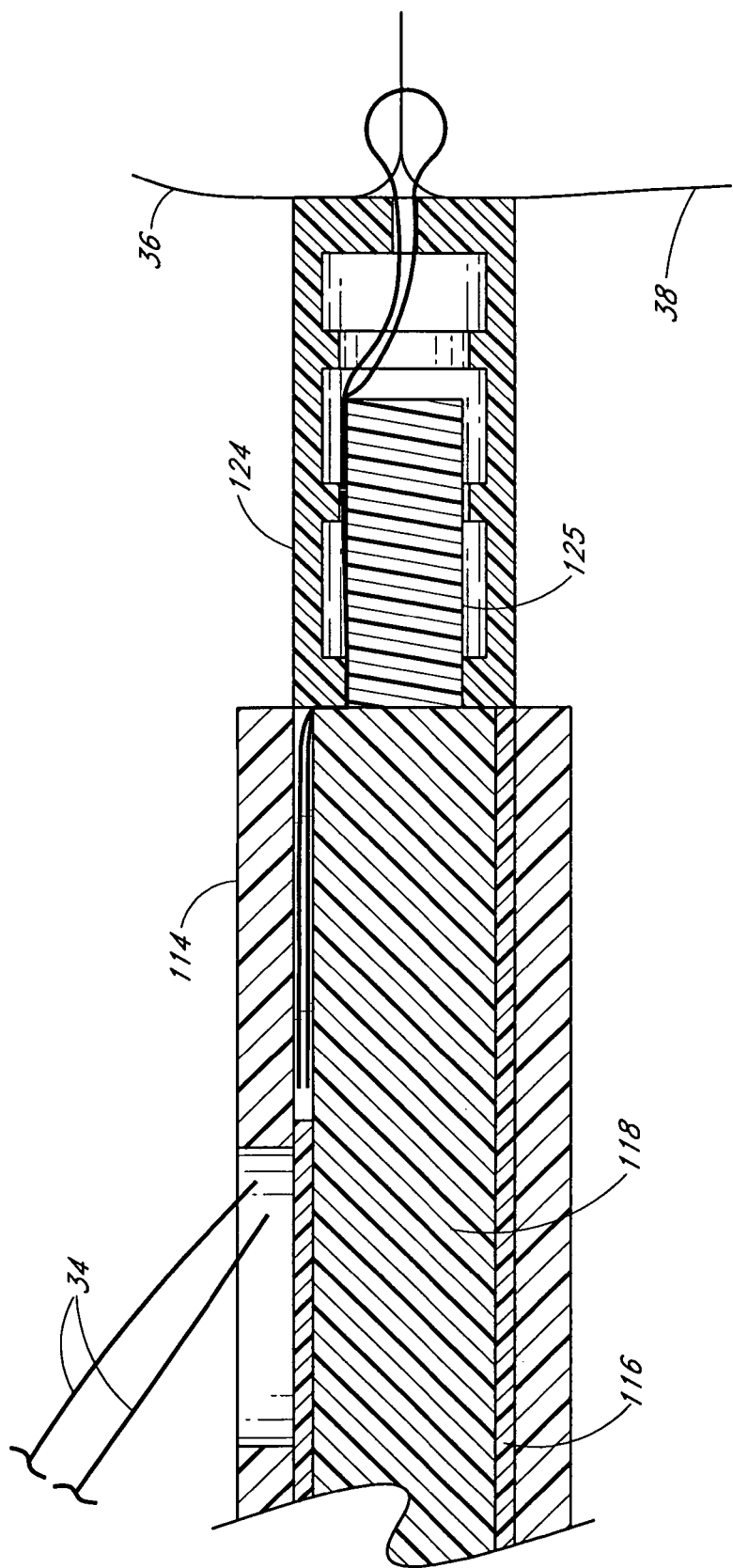
FIG. 22 illustrates the device of FIGS. 19-21, the push rod being further advanced, the intermediate tube also being advanced to eject the knot from the device and sever the suture portions.

FIGS. 19-23 illustrate one embodiment for placing a knot utilizing the knot placement device 100 described above. With reference to FIG. 19, a pair of sutures ends 40 and 42 may be passed through the loop 130 of threader 128. The threader is preloaded into the knot placement device 100 as described above. The tab 132 of threader 128 may be pulled proximally to dispose suture 34 in the device, as shown in FIG. 20. Suture 34 may be held in tension, by hand or otherwise, while the device 100 is advanced until the knot body 124 or shaft 104 contacts at least one of tissue portions 36 and 38, as illustrated in FIG. 20. The actuator 106 may be depressed to advance the push rod 118, thereby forcing the plug 126 distally into the knot body 124 and trapping suture 34 there between the plug 126 and the knot body 124, as shown in FIG. 21. The actuator may be further depressed until the cam 108 contacts the proximal end of intermediate tube 116, causing the intermediate tube 116 to contact knot body 124 and eject the knot from the shaft 104. As shown in FIG. 22, advancement of intermediate tube 116 may also cause cutting surface 123 to sever suture 34 where it extends out of opening 120. The knot placement device may then be removed, leaving the knot in place against the tissue portions, as shown in FIG. 24.

In one embodiment, the knot may be ejected from the shaft 104 while leaving the sutures 34 un-severed. For example, the knot may be ejected before the cutting surface 123 reaches the suture 34. In another embodiment, no intermediate tube is provided, and the suture may be cut manually.

Figure 23:
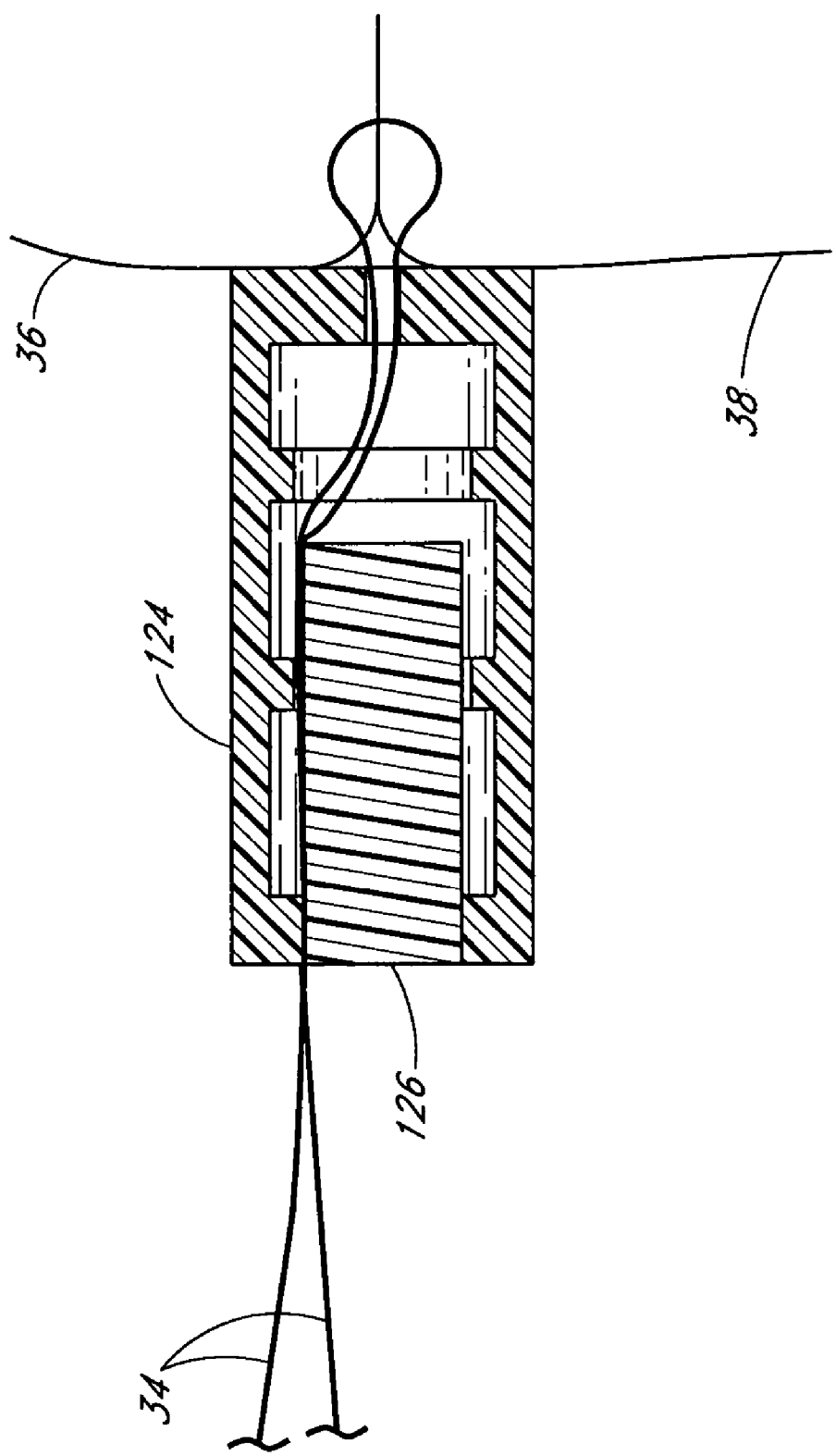
FIG. 23 illustrates the knot of FIGS. 19-22, in its final placement.
Figure 24:
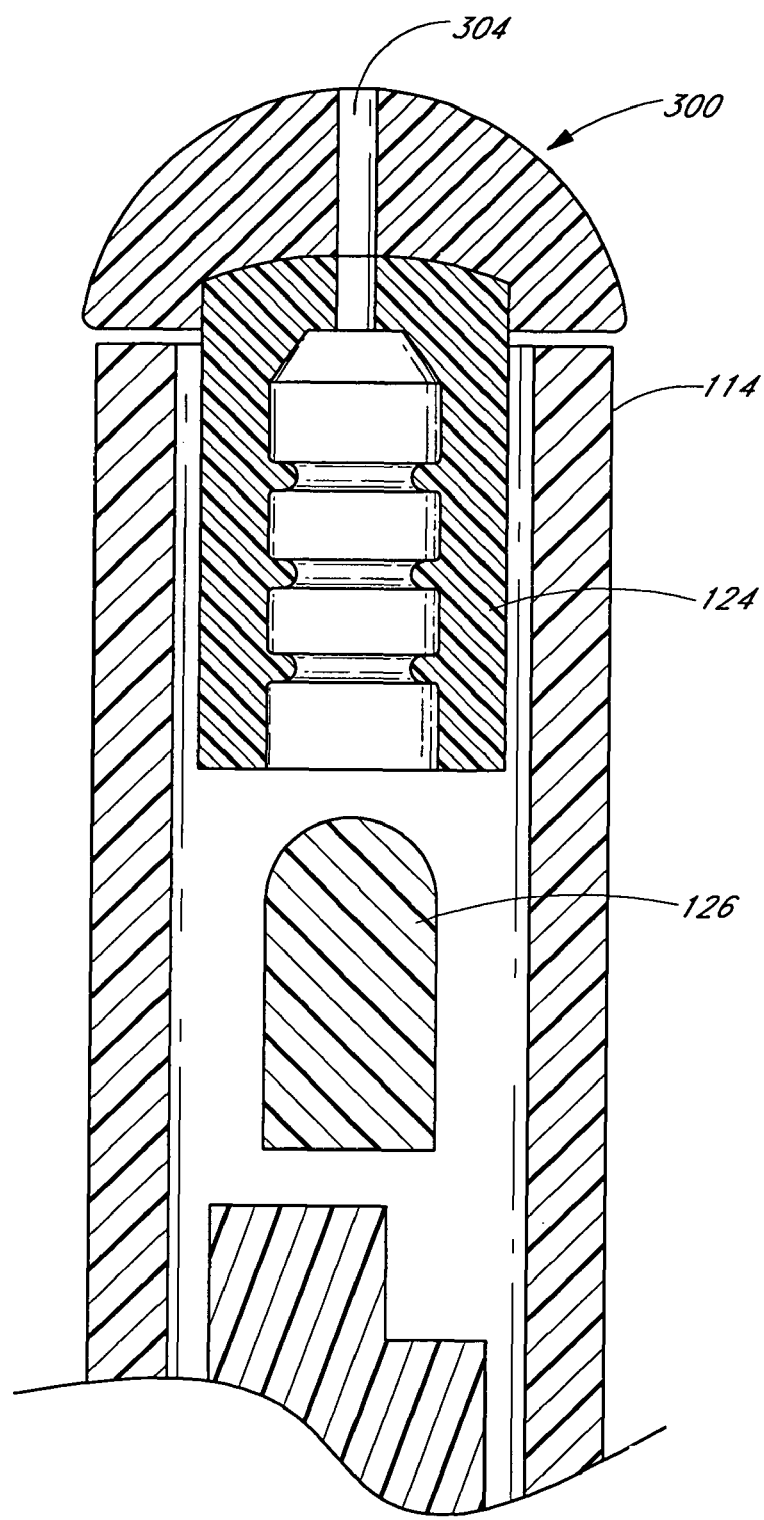
FIGS. 24 and 25 illustrate another embodiment of a knot having an atraumatic tip.

FIGS. 19-23 illustrate one embodiment for placing a knot utilizing the knot placement device 100 described above. With reference to FIG. 19, a pair of sutures ends 40 and 42 may be passed through the loop 130 of threader 128. The threader is preloaded into the knot placement device 100 as described above. The tab 132 of threader 128 may be pulled proximally to dispose suture 34 in the device, as shown in FIG. 20. Suture 34 may be held in tension, by hand or otherwise, while the device 100 is advanced until the knot body 124 or shaft 104 contacts at least one of tissue portions 36 and 38, as illustrated in FIG. 20. The actuator 106 may be depressed to advance the push rod 118, thereby forcing the plug 126 distally into the knot body 124 and trapping suture 34 there between the plug 126 and the knot body 124, as shown in FIG. 21. The actuator may be further depressed until the cam 108 contacts the proximal end of intermediate tube 116, causing the intermediate tube 116 to contact knot body 124 and eject the knot from the shaft 104. As shown in FIG. 22, advancement of intermediate tube 116 may also cause cutting surface 123 to sever suture 34 where it extends out of opening 120. The knot placement device may then be removed, leaving the knot in place against the tissue portions, as shown in FIG. 23.

The actuator 106 and cam 108 may also be provided with locking mechanisms that prevent the actuator 106 from returning to its original position. Further details are provided in application Ser. No. 11/235,751 filed Sep. 27, 2005, the entirety of which is hereby incorporated by reference. Such an embodiment may be advantageous to hold the push rod flush with the distal end of the outer tube to provide a surface that can be utilized to further advance and position the knot against tissue portions 36 and 38.

It will be appreciated that other embodiments are contemplated without use of the intermediate tube, but are still capable of severing the suture. For example, the push rod may be provided with portions of differing diameter. A distal, smaller diameter may be sized to engage the plug 126 to push the plug into the knot body 124. A proximal, larger diameter may be provided on the push rod, which includes a sharpened surface at the transition between the larger and smaller diameter sections. Once the smaller portion of the push rod pushes the plug 126 into the knot body 124, the larger portion of the push rod may engage the knot body 124 to push the knot out of the placement device, while the sharpened surface on the push rod may sever the suture.

In the embodiment described above, when the knot body 124 and the plug 126 as described above are secured together, suture portions extending through the inner cavity of the knot body from opening 136 to opening 138 will be fixedly secured therein, forming a knot. It will be appreciated that many other embodiments are possible for forming a knot, including various other shapes and configurations for the knot body and plug, as well as embodiments wherein only one component may be used to provide securement relative to a suture. It will also be appreciated that in those embodiments in which the knot comprises a knot body and plug, the plug may be located within the shaft proximally from the knot body or the knot body may be located within the shaft proximally from the plug.

Figure 11:
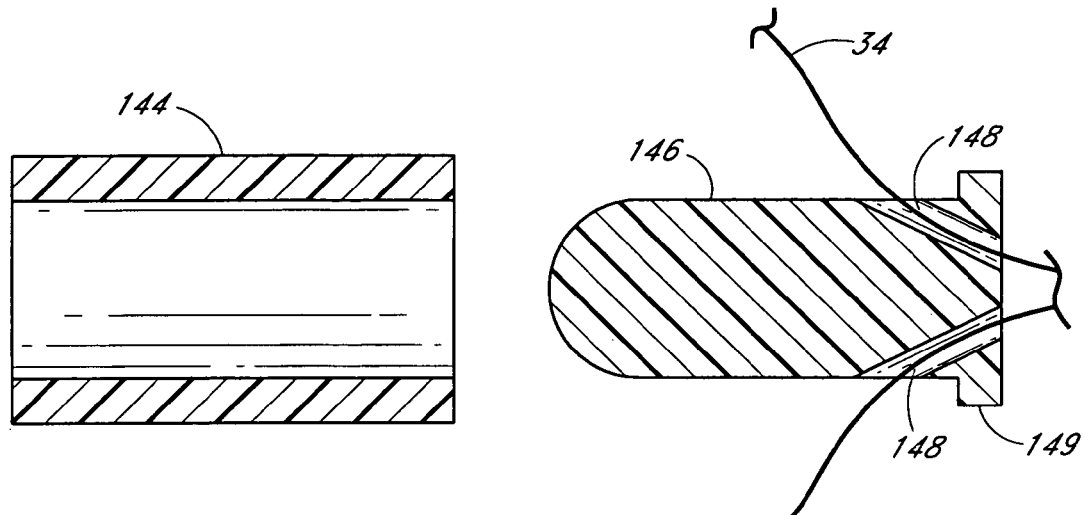
FIG. 11 is a cross-sectional side view of another embodiment of a knot.

For example, in another embodiment of a knot, shown in FIG. 11, a plug 146 is provided having a pair of holes 148 extending divergently from one end of the plug (e.g., a proximal end) to the diametrically opposed, outer surfaces of the plug. A shoulder 149 of increased outer diameter may be located at one end of plug 146 (e.g., the proximal end). When the plug 146 is inserted into a hollow knot body, the plug 146 and knot body 144 cooperate to secure the suture 34 therebetween.

Figure 12:
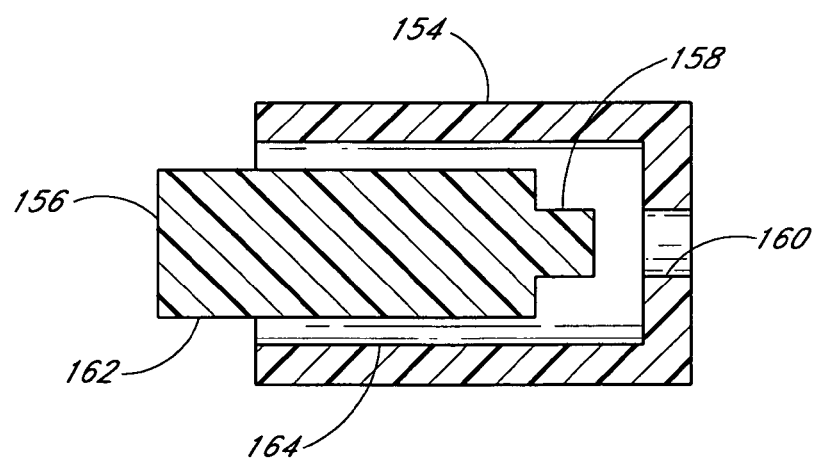
FIG. 12 is a cross-sectional side view of another embodiment of a knot.

In another embodiment, shown in FIG. 12, a plug 156 may comprise two sections having different outer diameters. A knot body 154 has an opening 136 with an inner surface 160. A surface 162 of plug 156 may have a smaller diameter than an interior surface 164 of knot body 154. A surface 158 of plug 156 may have a diameter such that surface 158 engages surface 160 of knot body 154 and cooperate to hold suture portions securely therein.

In another embodiment, shown in FIGS. 13 and 14, a plug 176 comprises a longitudinally-extending slot 178 such that plug 176 is generally fork-shaped. The slot 178 extends from the distal end partially to the proximal end. Suture 34 extends through the knot body 174, through the slot 178, and out from the plug 176, preferably on opposite sides of the plug 176. Insertion of the plug 176 into knot body 174 preferably causes compression of the slot to securely fix the suture portions within the slot. It will be appreciated that in this embodiment, the knot placement device can either be actuated to move the plug distally into the knot body, or alternatively, may be actuated to move the knot body distally over the plug.

Figure 15:
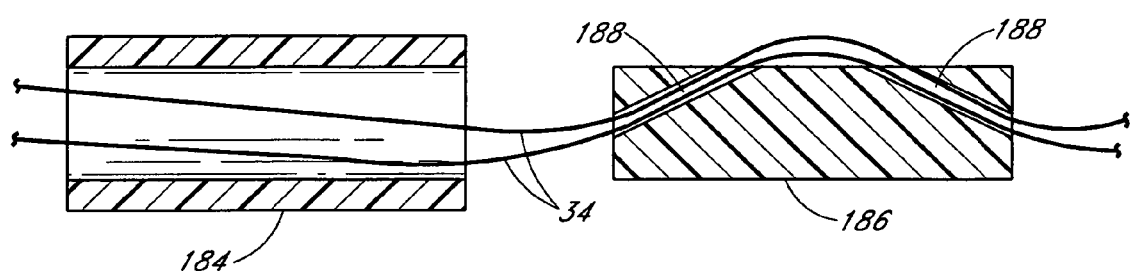
FIG. 15 is a cross-sectional side view of another embodiment of a knot.

In another embodiment, shown in FIG. 15, a pair of side holes 188 are provided at spaced locations along the length of a plug 186. Suture portions pass from an end hole at one end of the plug 186, outwardly through one of the side holes, and then inwardly back into the body of the plug and out an opposite end hole. When the knot body 184 is slid over the plug, either by being advanced distally over the plug or by having the plug advanced distally into the knot body, the suture 34 is secured relatively between the plug and the knot body.

Figure 16A:
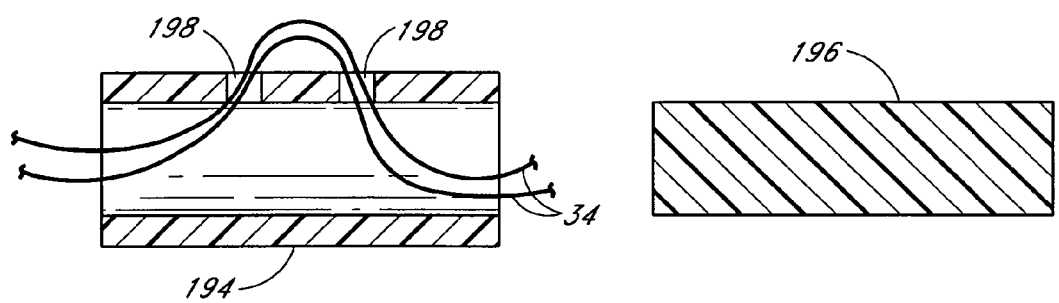
FIG. 16a is a cross-sectional side view of another embodiment of a knot and illustrating a routing of a suture through the knot body.
Figure 16B:
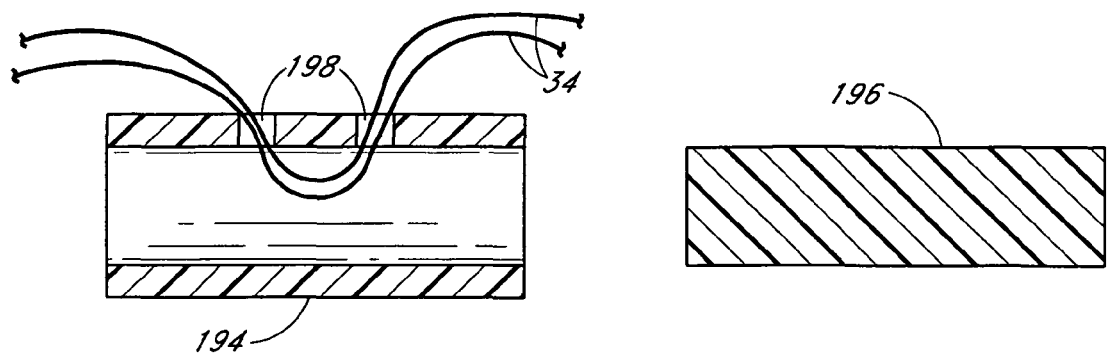
FIG. 16b is a cross-sectional side view of the embodiment of the knot of FIG. 16a and illustrating an alternative routing of a suture through the knot body.

In another embodiment, shown in FIGS. 16a and 16b, a knot body 194 comprises two side holes 198. Suture 34 may be routed through knot body 194 either from within the body, out through one of the side holes, and back into the body through the other side hole, as shown in FIG. 16a, or may be routed into one of the side holes from outside the body, into the body, and then out the other side hole, as shown in FIG. 16b. In either embodiment, a plug 196 may then be used to secure the suture relative to the knot body.

Figure 17A:
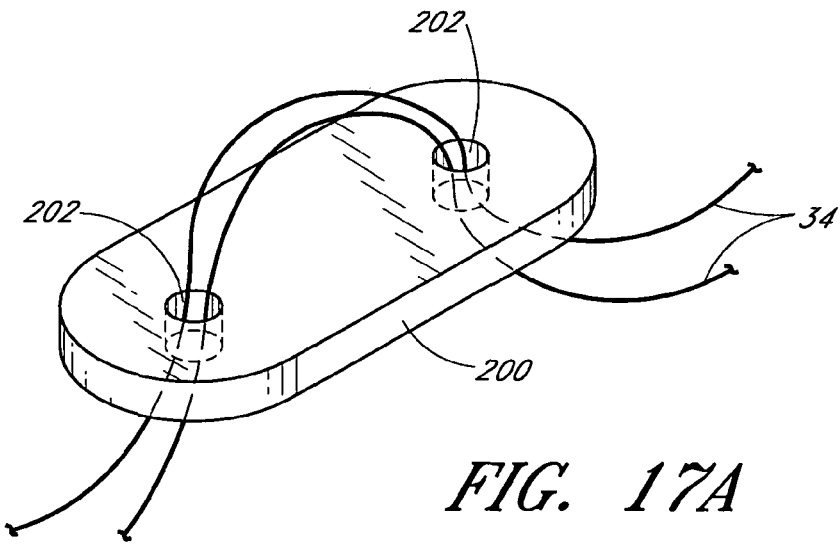
FIG. 17a is a perspective view of another embodiment of a knot.
Figure 17B:
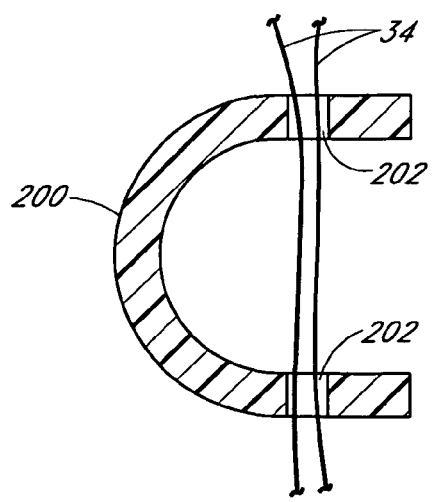
FIG. 17b is a cross-sectional side view of the embodiment of a knot shown in FIG. 17.

In another embodiment, shown in FIGS. 17a and 17b, a knot 200 comprises a single component or knot body. A plate, ring or other structure, such as a flat resilient member, may be provided with two holes 202. As shown in FIG. 17b, the plate is bent to form a "U" shape, to allow the suture 34 to be passed therethrough. The plate may be made of an elastic or shape memory material which springs back to its flattened configuration, shown in FIG. 17a, which locks the suture in place relative to the plate. Other embodiments are also contemplated in which suture portions are provided through a tortuous path of a knot body. A threader as described above may be used to guide the suture portions through the knot body while it is positioned within a knot placement device. Once ejected from the knot placement device, the knot body may assume a different configuration which locks the suture in place relative to the knot body.

Figure 18A:
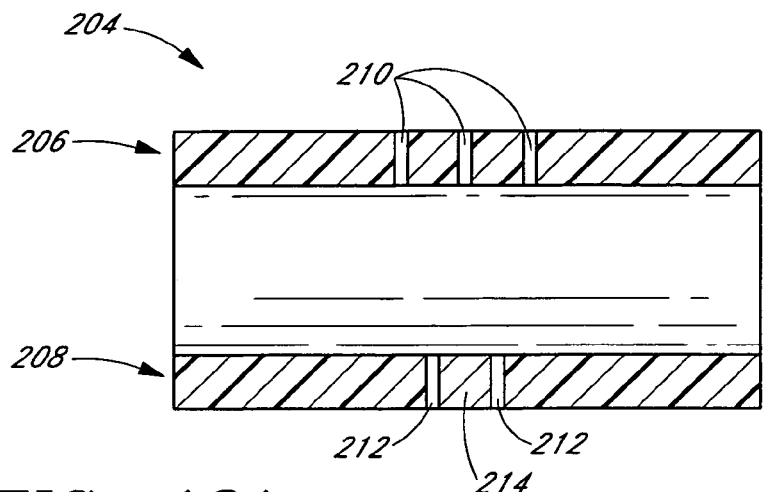
FIG. 18a is a cross-sectional side view of another embodiment of a knot.
Figure 18B:
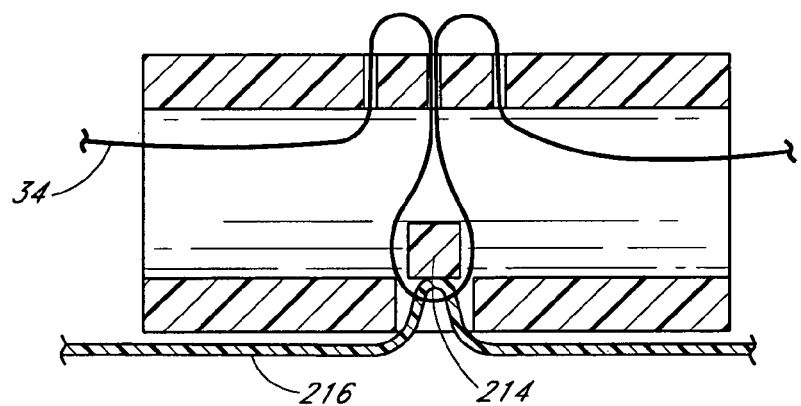
Figure 18C:
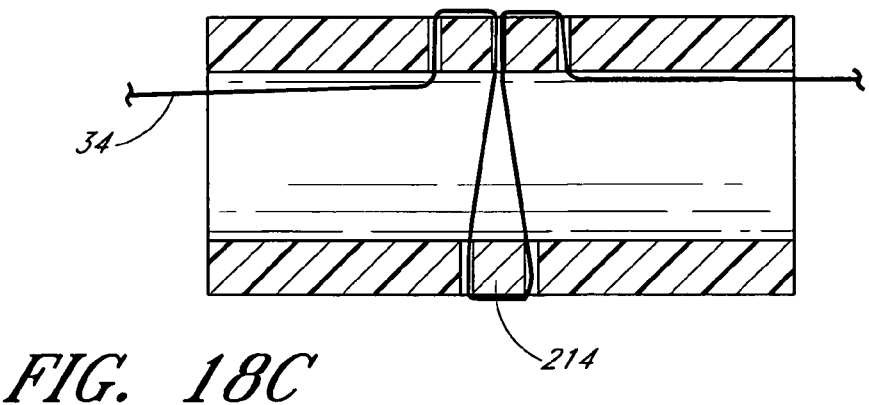
FIG. 18c is a cross-sectional side view of the knot of FIGS. 18a-18b.

In another embodiment, shown in FIGS. 18a, 18b, and 18c, a knot 204 comprises a tube having an upper wall 206 and a lower wall 208. The upper wall comprises three linearly-spaced apertures 210. The lower wall comprises two apertures 212 to create a displaceable section 214 in the lower wall 208. The displaceable section 208 is displaced toward the center of the knot 204 by any suitable means, such as a curved rod 216 as illustrated in FIG. 18b. A suture 34 is threaded in and out of the apertures 210 in the upper wall and around the displaceable section 214 of the lower wall. As the knot 204 is ejected from the knot placement device, the displaceable section 214 is allowed to move toward its original position to more surely secure the suture 34 within the knot 204 as illustrated in FIG. 18c.

Figure 25:
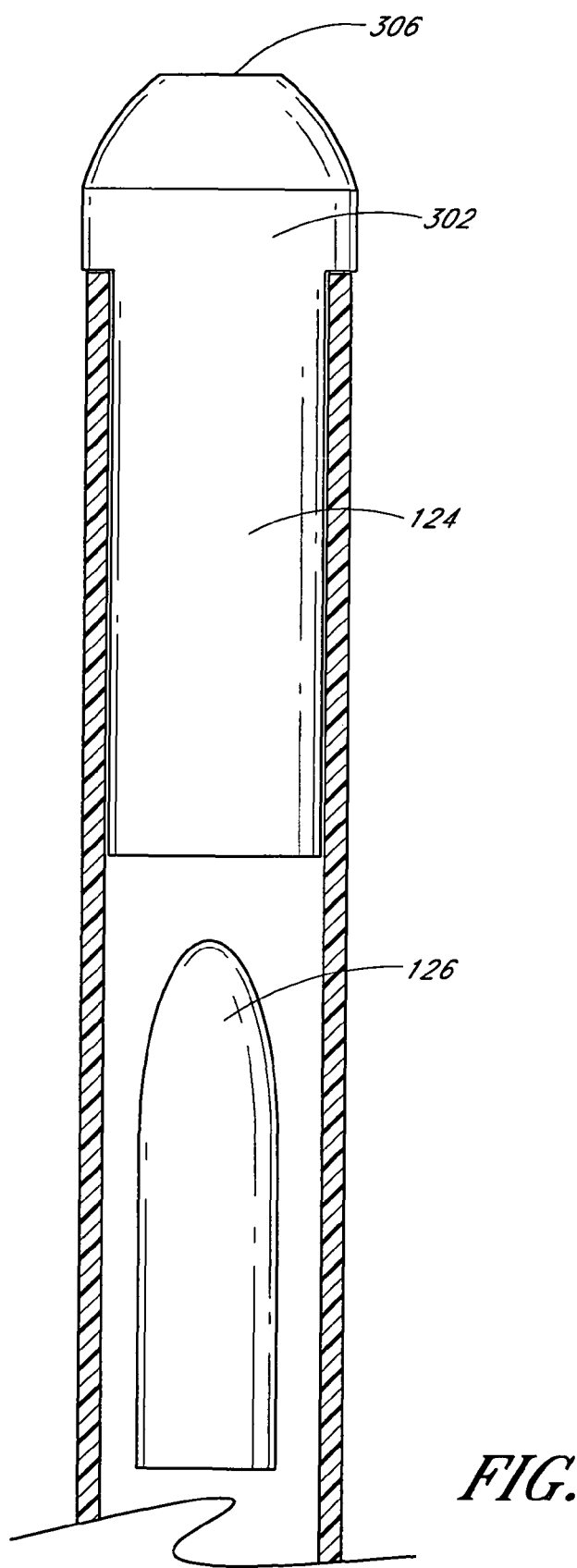

In another embodiment, shown in FIGS. 24 and 25, a knot comprises a knot body 124 and a plug 126 such as described above, but with the knot body having an atraumatic tip 300. The tip 300 may be rounded and have an outer diameter about the same as that of the outer tube 114. As shown more particularly in FIG. 25, the tip may have a flat transition 302 as well. The tip 300 may be integrally formed with the knot body 124 or may be separately attached. As illustrated, the tip 300 may have an aperture 304 extending axially through the tip, opening to the cavity inside the knot body. When the knot is delivered into a patient as described above, the atraumatic tip prevents damage to the patient.

Various other embodiments are contemplated for the knot. For example, a knot may simply comprise a tube with a sufficiently small inner diameter through which suture portions may be positioned and held. In another embodiment not shown, the plug may comprise a shoulder located near its proximal end having an increased outer diameter. The shoulder may not be inserted into the knot body, but may be used to push the knot out of the placement device once the plug has been inserted into the knot body.

It should be understood that certain variations and modifications of this invention will suggest themselves to one of ordinary skill in the art. The scope of the present invention is not to be limited by the illustrations or the foregoing descriptions thereof.

What is claimed is:

1. A method for securing two suture portions extending from an opening in the body, comprising:
   positioning said two suture portions within a knot body;
   advancing said knot body to a location near tissue adjacent the opening by advancing a knot placement device to said location near tissue adjacent the opening, said knot placement device comprising
      an outer tube releasably holding said knot body,
      an intermediate tube concentrically and slidably disposed within said outer tube and having a length at least as long as said outer tube, and
      a push rod and a plug slidably disposed within said intermediate tube such that said plug is positioned distally of said push rod;
   using said push rod, advancing said plug alongside of said suture portions toward said knot body to fixedly secure said suture portions between said knot body and an outer surface of said plug by pushing said plug using said push rod; and
   using said intermediate tube, ejecting said plug and knot body fixedly securing said suture portions from said knot placement device by pushing said knot body using said intermediate tube.

2. The method of claim 1, further comprising applying tension to said suture portions while advancing the knot body.

3. The method of claim 1, wherein the suture portions extend from two tissue portions adjacent an incision of a wound site.

4. The method of claim 1, wherein the suture portions are positioned initially within the knot body, and the plug is inserted into the knot body.

5. The method of claim 1, wherein positioning said two suture portions within a knot body comprises:
   inserting a threader, having proximal and distal ends and a hole in the distal end, through said knot body;
   threading said two suture portions through the hole in said threader; and
   proximally retracting said threader through said knot body.

6. The method of claim 1, further comprising cutting the suture portions proximal to a proximal end of the knot body.

7. The method of claim 5, wherein the step of inserting said threader comprises inserting the threader through a side hole in said outer tube of said knot placement device, and further comprising the step of proximally retracting said threader through said side hole to draw said suture portions through said side hole.

8. The method of claim 1, further comprising cutting the suture portions proximal to a proximal end of the knot body, wherein said cutting comprises distally advancing a cutting surface of said knot placement device.

9. The method of claim 8, wherein said cutting surface is disposed on said intermediate tube.

10. The method of claim 9, wherein said cutting surface is formed on a proximal end of a slot formed in said intermediate tube.

11. The method of claim 9, wherein said steps of cutting the suture portions and advancing said plug and knot body fixedly securing said suture portions are performed simultaneously.

12. The method of claim 1, wherein said push rod and said intermediate tube are advanced by a cam disposed at proximal ends of said push rod and said intermediate tube and said cam begins advancing said push rod before advancing said intermediate tube.

* * * * *